(12) United States Patent
Noack (10) Patent No.: US 11,083,829 B2
(45) Date of Patent: Aug. 10, 2021

(54) MEDICAL TREATMENT DEVICE AND METHOD FOR MONITORING A MEDICAL TREATMENT DEVICE

(71) Applicant: FRESENIUS MEDICAL CARE DEUTSCHLAND GMBH, Bad Homburg (DE)

(72) Inventor: Joachim Noack, Bad Neustadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 241 days.

(21) Appl. No.: 16/094,885

(22) PCT Filed: Apr. 11, 2017

(86) PCT No.: PCT/EP2017/058706
§ 371 (c)(1),
(2) Date: Oct. 19, 2018

(87) PCT Pub. No.: WO2017/182337
PCT Pub. Date: Oct. 26, 2017

(65) Prior Publication Data
US 2019/0125950 A1 May 2, 2019

(30) Foreign Application Priority Data

Apr. 22, 2016 (DE) .................... 10 2016 004 908.1

(51) Int. Cl.
*A61M 1/36* (2006.01)
*A61M 1/14* (2006.01)
*A61M 1/16* (2006.01)

(52) U.S. Cl.
CPC ............ *A61M 1/1613* (2014.02); *A61M 1/14* (2013.01); *A61M 1/3639* (2013.01);
(Continued)

(58) Field of Classification Search
CPC ........ A61M 1/14; A61M 1/16; A61M 1/1613; A61M 1/3639; A61M 2205/15;
(Continued)

(56) References Cited

U.S. PATENT DOCUMENTS

| 5,087,245 A | 2/1992 | Doan |
| 2003/0136181 A1 | 7/2003 | Balschat et al. |

(Continued)

FOREIGN PATENT DOCUMENTS

| DE | 10149809 C1 | 5/2003 |
| WO | 2008024908 A2 | 2/2008 |
| WO | 2012151077 A2 | 11/2012 |

OTHER PUBLICATIONS

International Preliminary Report on Patentability issued in corresponding International Patent Application No. PCT/EP2017/058706 dated Oct. 23, 2018 (7 pages).

(Continued)

*Primary Examiner* — Patrick Orme
(74) *Attorney, Agent, or Firm* — Kilyk & Bowersox, P.L.L.C.

(57) ABSTRACT

The invention relates to a medical treatment device comprising a fluid system, which has a monitoring apparatus 27 for monitoring the treatment device, wherein the monitoring apparatus 27 is configured such that monitoring is based on the evaluation of the pressure in the fluid system of the medical treatment device. The invention further relates to a method for monitoring a medical treatment device, in which monitoring is based on the evaluation of the pressure in the fluid system. The treatment device is characterised by a compliance-determining apparatus 28 for determining the compliance in the fluid system, part of the fluid system or parts of the fluid system, wherein the compliance-determining apparatus 28 cooperates with the monitoring apparatus (Continued)

27 in such a manner that the pressure-based monitoring takes place depending on the compliance of the fluid system.

15 Claims, 6 Drawing Sheets

(52) U.S. Cl.
CPC . *A61M 2205/15* (2013.01); *A61M 2205/3331* (2013.01); *A61M 2205/70* (2013.01)

(58) Field of Classification Search
CPC ...... A61M 2205/3331; A61M 2205/70; A61M 2205/52
See application file for complete search history.

(56) References Cited

U.S. PATENT DOCUMENTS

| | | | |
|---|---|---|---|
| 2007/0058412 A1* | 3/2007 | Wang | A61M 5/16809 365/120 |
| 2012/0312726 A1 | 12/2012 | Gagel | |
| 2013/0028788 A1* | 1/2013 | Gronau | A61M 1/3413 422/44 |
| 2013/0233314 A1 | 9/2013 | Jafari et al. | |

OTHER PUBLICATIONS

International Search Report issued in corresponding International Patent Application No. PCT/EP2017/058706 (with English translation) dated Jun. 26, 2017 (6 pages).

* cited by examiner

MEDICAL TREATMENT DEVICE AND METHOD FOR MONITORING A MEDICAL TREATMENT DEVICE

This application is a National Stage Application of PCT/EP2017/058706, filed Apr. 11, 2017, which claims priority to German Patent Application No. 10 2016 004 908.1, filed Apr. 22, 2016.

The invention relates to a medical treatment device which has a monitoring apparatus which is configured such that monitoring is based on the evaluation of the pressure in the fluid system. The invention further relates to a method for monitoring a medical treatment device, in which monitoring is based on the evaluation of the pressure in the fluid system.

In dialysis as an example of extracorporeal blood treatment, the blood to be treated flows in an extracorporeal blood circuit through the blood chamber of a dialyser divided by a semi-permeable membrane into the blood chamber and a dialysate chamber, while dialysate flows through the dialysate chamber of the dialyser in a dialysate system. The extracorporeal blood circuit has a blood supply line, which leads to the blood chamber, and a blood removal line, which comes from the blood chamber, and the dialysate system has a dialysate supply line leading to the dialysate chamber and a dialysate removal line coming from the dialysate chamber. Part of the fluid system comprising the dialyser and the blood lines can generally be designed for single use. The line portions of the fluid system that are filled with blood during blood treatment can be in the form of a tube set and/or cassette. For the blood treatment, the tube set or cassette is inserted into the blood-treatment device or fixed in or to the treatment device. However, the dialysate system, which comprises the dialysate lines, can also be in the form of a replaceable unit (disposable).

A blood pump is provided in the extracorporeal blood circuit for conveying the blood, and at least one dialysate pump is provided in the dialysate system for conveying the dialysate. The fresh dialysate is made available in a dialysate source and used dialysate is discharged into a drain. The blood-treatment devices additionally have a balancing unit for balancing fresh and used dialysate, and an ultrafiltration apparatus having an ultrafiltration pump for removing ultrafiltrate from the fluid system. Also known are dialysis devices in which the balancing apparatus and the ultrafiltration apparatus for example can be combined by controlling the incoming and outgoing flows by means of pumps.

It is known to check the tightness of a fluid system that encloses a closed volume by means of pressure hold tests, in which an excess pressure or a negative pressure is established in the fluid system. If the pressure does not fall below a specific limiting value or rise above a specific limiting value in a specified time period, it can be concluded that the fluid system is tight.

EP 1 327 457 A1 discloses a blood-treatment device having a monitoring apparatus for detecting a leak in the fluid system of the treatment device. The monitoring apparatus has a pressure sensor for measuring the pressure in the fluid system. During the blood treatment, the pressure in the fluid system is measured continuously, the leakage rate is determined from a possible change in the pressure, the leakage volume is calculated from the leakage rate, and the leakage volume is compared with a specified limiting value.

Pressure changes in the fluid system of a blood-treatment device are also detected in order to control the treatment device. Reliable monitoring or control of the blood-treatment device therefore requires correct evaluation of the measured pressure changes. In practice, the evaluation of pressure changes for monitoring or controlling the treatment device has not been without problems. It is difficult in practice to set suitable limiting values for monitoring the device because, when setting suitable limiting values, it is necessary to take account of the fact that the dialysers and tube sets or cassettes that are used can have different properties, which can influence pressure changes.

The object of the invention is to provide a medical treatment device, in particular an extracorporeal blood-treatment device, which permits improved pressure-based monitoring. An additional object of the invention is to provide a method which permits improved pressure-based monitoring.

These objects are achieved according to the invention by the features of the independent claims. The dependent claims relate to advantageous embodiments of the invention.

The device according to the invention and the method according to the invention permit improved pressure-based monitoring even when different dialysers and/or tube lines are used, without it being necessary to enter new limiting values or parameters for the monitoring process. The medical treatment device has at least one pump for conveying at least one liquid into and/or out of a fluid system. The pump can be a blood pump for conveying blood in an extracorporeal blood circuit during the treatment, a dialysate pump for conveying dialysate in a dialysate system, a pump for filling a balancing system, an ultrafiltration pump or a substitution pump for conveying a liquid (substituate) into the blood-side fluid system. In preparation for the blood treatment, the blood pump can also be used for filling the fluid system. The liquid for filling the fluid system can also be provided in a bag. The pumps can be peristaltic pumps which, owing to their occlusive function, can themselves serve as valves, so that a closed volume can be created in the fluid system.

The treatment device additionally has a monitoring apparatus which is configured such that monitoring is based on evaluation of the pressure in the fluid system, part of the fluid system or parts of the fluid system. The monitoring apparatus can also be part of a control apparatus for controlling the treatment device depending on the pressure. One or more pressure sensors are provided for measuring the pressure. The pressure sensor or sensors can also be provided in the treatment device for different purposes.

For receiving at least part of the fluid system, the medical treatment device can have at least one receiver, so that the fluid system or parts of the fluid system can be inserted into the blood-treatment device or fixed thereto.

A fluid system is understood as meaning all components which enclose a volume or a plurality of volumes which are able, as intended, to receive one or more fluids during operation of the medical treatment device. The volume or parts of the volume can be sealed off in a fluid-tight manner from the surroundings by suitable members, for example tube clamps, closing caps, etc. The fluid system can also comprise a plurality of parts, for example a plurality of tube sets or cassettes. If the fluid system consists of a plurality of parts, a plurality of receivers, into which the individual parts can be inserted, can be provided.

In the case of an extracorporeal blood-treatment device, the fluid system can comprise the dialyser, the extracorporeal blood circuit and the dialysate system. Such fluid systems and receivers belong to the prior art. If the fluid system is configured as a single-use tube set or as a cassette, the blood-treatment device can act on the tube set or the cassette by means of actuating members, for example can clamp tube lines at given points in the fluid system.

The treatment device is distinguished by a compliance-determining apparatus for determining the compliance in the fluid system, part of the fluid system or parts of the fluid system, wherein the compliance-determining apparatus cooperates with the monitoring apparatus in such a manner that pressure-based monitoring takes place depending on the compliance of the fluid system.

In practice, it has been shown that the compliance of the fluid system influences pressure changes to a significant extent. The principle of the invention is, therefore, to determine the compliance of the fluid system, part of the fluid system or parts of the fluid system and to take the compliance into consideration when setting limiting values or parameters for monitoring the medical treatment device. In the treatment device according to the invention, the compliance can be used as a selection criterion for setting limiting values or parameters. For example, compliance-dependent sets of limiting values or parameters for operating the treatment device can be selected automatically.

In the device according to the invention or the method according to the invention, a change in the compliance, for example due to air which may be trapped in the fluid system, can have either no influence or less of an influence on the pressure-based monitoring than if the compliance were not taken into consideration, since monitoring is carried out depending on the compliance. In a blood-treatment device, a non-ventilated dialyser, for example, can make an important contribution to the compliance of the system. In practice, it may be that the dialyser has not been ventilated or has not been ventilated completely, individual types of dialyser being easier or more difficult to ventilate. This is not a disadvantage in the case of the device according to the invention or the method according to the invention, however, since the compliance is taken into consideration when monitoring. The properties of different tube sets or cassettes therefore cannot influence the monitoring.

How the treatment device is monitored is not important for the invention, all that is relevant is that pressure-based monitoring takes place. In that respect, the monitoring apparatus can have different configurations. The compliance-determining apparatus and the monitoring apparatus can be in the form of separate units or can be part of the central control and arithmetic unit of the treatment device.

One embodiment of the medical treatment device provides a treatment mode and a preparation mode, preceding the treatment, in preparation for the treatment. A treatment mode is understood as meaning the operating state of the treatment device in which the actual treatment takes place. In a blood-treatment device, this operating state is characterised in that the blood-side part of the fluid system is filled with blood.

Before the blood-treatment device is started up, the blood-side part of the fluid system is not filled. In preparation for the blood treatment, the blood-side part of the fluid system is first filled with a flushing liquid or preparation liquid (frequently referred to as the priming liquid).

The monitoring apparatus can be configured such that the determination of the compliance takes place in the preparation mode and the compliance-dependent, pressure-based monitoring takes place in the preparation mode and/or the treatment mode. This has the advantage that the determination of the compliance does not take place during treatment, when part of the fluid system is filled with blood. Also, the treatment does not have to be interrupted. When the dialyser of a blood-treatment device is part of the fluid system, the compliance can additionally be determined more easily by the known methods, since a pressure equalisation across the membrane of the dialyser, which is necessary for the known methods, can take place more quickly in the preparation mode, when the dialyser is filled with flushing liquid. The actual pressure-based monitoring can take place in the preparation mode before and/or during the blood treatment, for which purpose the treatment does not need to be interrupted. One embodiment provides that the monitoring apparatus is configured such that the compliance-dependent, pressure-based monitoring takes place only in the treatment mode, and the compliance is determined in the preparation mode.

The monitoring apparatus can be configured such that the volume of a liquid enclosed in the fluid system, part of the fluid system or parts of the fluid system is changed and the compliance in the fluid system, part of the fluid system or parts of the fluid system is determined on the basis of the pressure change in the fluid system, part of the fluid system or parts of the fluid system resulting from the change in volume. To that end, a specified volume of liquid can be supplied to the fluid system, part of the fluid system or parts of the fluid system, or a specified volume of liquid can be removed from the fluid system, part of the fluid system or parts of the fluid system, it being possible for the compliance in the fluid system, part of the fluid system or parts of the fluid system to be determined on the basis of the pressure change in the fluid system, part of the fluid system or parts of the fluid system resulting from the supply or removal of liquid. The pressure changes thereby increase as the compliance falls or fall as the compliance increases, that is to say the greater the flexibility, or the lower the rigidity, of the system, the smaller the pressure changes. For example, the pressure changes are relatively small if the walls of the tube lines or cassette deform to a relatively large extent when liquid is supplied or removed. When liquid is removed from the fluid system, the pressure in the system does not need to be increased, so that a specific limit pressure cannot be exceeded. The intention is that the pressure change lies in the region of the particular operating point of the treatment device.

The monitoring apparatus can be a tightness-monitoring apparatus which is configured such that the amount of change in the pressure in a specified time interval is compared with a specified limiting value, it being concluded that the system is not tight if the amount of change in the pressure is greater than the specified limiting value. Where there is a pressure drop by a specified value, it can be concluded, for example, depending on the compliance, that the system is not tight. The compliance-determining apparatus cooperates with the tightness-monitoring apparatus in such a manner that the limiting value for the change in pressure is set depending on the compliance.

A fluid system having greater compliance, for example, generally requires a lower limiting value to be set than a fluid system having lower compliance. The limiting value can be set, for example, by calculating the limiting value using an equation that describes the dependence of the limiting value on the compliance, or by selecting a limiting value from specified limiting values depending on the compliance. The tightness-monitoring apparatus can also be configured such that a correction factor for a limiting value assumed in the case of a rigid fluid system is ascertained, a smaller correction factor being ascertained for greater compliance than for lower compliance.

In one embodiment, the compliance-determining apparatus is configured such that the ratio of the compliance in a first part of the fluid system and the compliance in a second part of the fluid system is determined, and the compliance in the second part of the fluid system is determined from the compliance in the first part of the fluid system and the ratio of the compliance in the first and second part of the fluid system, or the compliance in the first part of the fluid system is determined from the compliance in the second part of the fluid system and the ratio of the compliance in the first and second part of the fluid system. This has the advantage that the compliance in only one part of the fluid system must be known. If the compliance in part of the fluid system is to be determined, the determination can be carried out in a different part in which the compliance can be determined more easily and/or reliably.

In this embodiment, the apparatus for determining the compliance can be configured such that the ratio of the compliance in the first and second part of the fluid system is determined by, determining the ratio of the pressure change in the first part of the fluid system and the pressure change in the second part of the fluid system in the case of a pressure equalisation between the first and second part of the fluid system. An advantage of this embodiment can come to bear if the compliance in the first part of the fluid system cannot be determined easily or reliably. This can be the case in an extracorporeal blood-treatment device when the compliance is to be determined in the part of the fluid system that comprises the blood chamber of the dialyser as well as the blood supply line and blood removal line, because the compliance should not be determined in a fluid system filled with blood. The embodiment therefore provides for the compliance to be determined in a different part of the fluid system of the blood-treatment device that can be a part of the fluid system that is not filled with blood, in particular during the preparation phase of the blood treatment, in which the blood-side fluid system is not yet filled with blood. Liquid can be pumped out of that part of the fluid system that can be filled with a liquid, for example dialysate, by means of the dialysate pump or the ultrafiltrate pump, in order to bring about a pressure change in the system. The dialysate can then be diverted into the drain, for example. It can also be advantageous to determine the compliance in a different part of the fluid system first if a specific volume of liquid can be supplied or removed precisely in order to determine the compliance only in the other part of the fluid system.

The invention will be described in detail below with reference to the figures, in which.

The invention will be described on the basis of an example of an extracorporeal blood-treatment device. However, the invention is not limited to the embodiment of the described blood-treatment device but can also relate to other embodiments which are known to a person skilled in the art. With reference to the figures, only the components of the blood-treatment device that are relevant for the invention are described. Even when specific embodiments are described, the parts can also have other configurations, providing they have the same function, for example a clamp or a peristaltic pump can be provided instead of a valve for shutting off a line. Furthermore, not all the relevant components have to be present.

Figure 1:
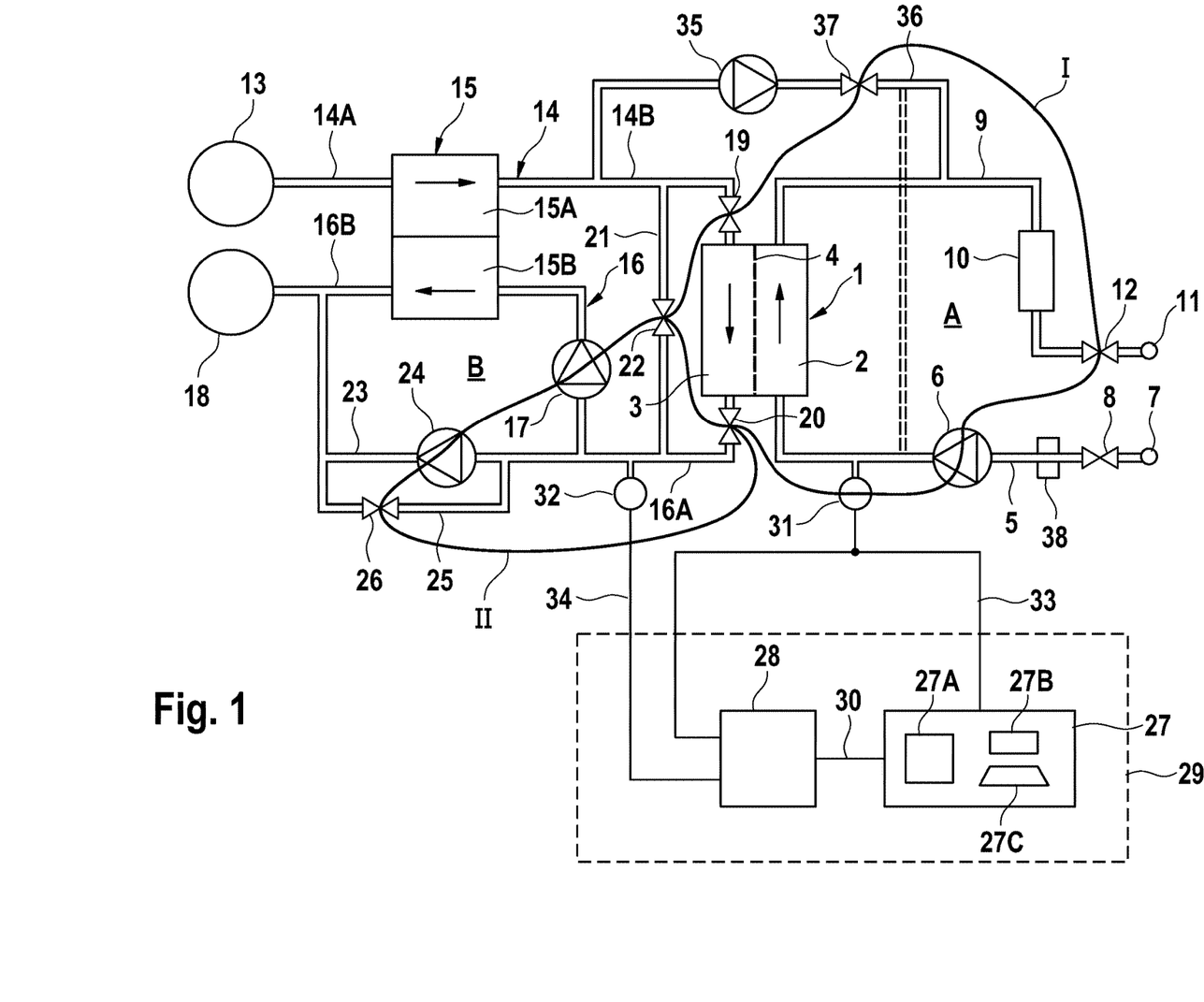
FIG. 1 shows components of an embodiment of a blood-treatment device according to the invention.

FIG. 1 is a highly simplified schematic view of the components of a blood-treatment device. The blood-treatment device comprises an extracorporeal blood circuit A and a dialysate system B. The extracorporeal blood circuit A and the dialysate system B form, together with the dialyser 1, the fluid system of the extracorporeal blood-treatment device. The fluid system or parts of the fluid system can be in the form of disposables for single use. In the following, the blood-treatment device will be described in the equipped state, in which the disposable(s) has/have been inserted into or fixed to the blood-treatment device.

The dialyser 1 has a blood chamber 2 and a dialysate chamber 3, which are separated by a semi-permeable membrane 4. A blood supply line 5, in which a blood pump 6 is provided, leads from an arterial patient port 7 to the inlet of the blood chamber 2. An arterial valve 8 can be located in the blood supply line 5, upstream of the blood pump 6. A blood removal line 9, in which a liquid chamber 10 can be arranged, leads from the outlet of the blood chamber 2 to a venous patient port 11. A venous valve 12 is situated in the blood removal line 9, downstream of the liquid chamber 10.

The dialysate system B has a dialysate source 13 for providing fresh dialysate, which dialysate source is connected via a first portion 14A of a dialysate supply line 14 to the inlet of one chamber 15A of a balancing unit 15. The second portion 14B of the dialysate supply line connects the outlet of one chamber 15A of the balancing unit 15 to the inlet of the dialysate chamber 3.

The dialysate can be used as a flushing or preparation liquid. The outlet of the dialysate chamber 3 is connected via a first portion 16A of a dialysate removal line 16 to the inlet of the other chamber 15B of the balancing unit 15. In the first portion 16A of the dialysate removal line 16, there is a dialysate pump 17. The outlet of the other chamber 15B of the balancing unit 15 is connected via the second portion 16B of the dialysate removal line 16 to a drain 18. The balancing unit 15 can have additional chambers.

In the dialysate supply line 14, there is a valve 19 upstream of the dialysate chamber 3, and in the dialysate removal line 16, there is a valve 20 downstream of the dialysate chamber 3. The valves 19, 20 can be electromagnetically actuable valves. The second portion 14B of the dialysate supply line 14 can be connected via a first bypass line 21, in which a first bypass valve 22 is provided, to the first portion 16A of the dialysate removal line 16. An ultrafiltrate line 23, in which an ultrafiltrate pump 24 is provided, leads from the first portion 16A of the dialysate removal line 16 to the second portion 16B of the dialysate removal line 16. A second bypass line 25, in which a second bypass valve 26 is provided, can lead from a portion of the ultrafiltrate line 23 that is upstream of the ultrafiltrate pump 24 to a portion of the ultrafiltrate line 23 that is downstream of the ultrafiltrate pump 24. The blood pump 6, the dialysate pump 17 and the ultrafiltrate pump 24 can be occlusive pumps. If the pumps are occlusive pumps, valves for creating a closed volume can be omitted.

In the present embodiment, the blood supply and removal lines 5, 9 of the extracorporeal blood circuit A are components of a replaceable blood tube set, and the dialysate supply and removal lines 14, 16 of the dialysate system B are fixed components of the hydraulic part of the blood treatment device. The blood tube set and the dialyser 1 are intended for single use and are inserted into receivers (not shown). Instead of a tube set, it is also possible to provide a replaceable cassette in which channels for the liquid, in particular the supply and removal of blood, are formed. The receiver for the dialyser can be a holder. Receivers for the blood supply line 5 can be formed in or on the blood pump 6.

The blood-treatment device has a monitoring apparatus 27 and a compliance-determining apparatus 28 for determining the compliance. The monitoring apparatus 27 and the compliance-determining apparatus 28 can be part of a common apparatus, which can also be part of a central control and arithmetic apparatus 29.

The monitoring apparatus 27 and/or the compliance-determining apparatus can have, for example, a general processor, a digital signal processor (DSP) for continuously processing digital signals, a microprocessor, an application-specific integrated circuit (ASIC), an integrated circuit consisting of logic elements (FPGA), or other integrated circuits (IC) or hardware components for carrying out the individual method steps. A data-processing program (software) can run on the hardware components in order to carry out the method steps. A plurality or combination of the various components is also possible.

The monitoring apparatus 27 and the compliance-determining apparatus 28 are connected to the pumps 6, 17, 24, the valves 8, 12, 19, 20 and the bypass valves 22, 26 via control or data lines (not shown), so that the flow rates of the pumps can be set and the valves and bypass valves can be actuated. The valves and bypass valves have actuating members (not shown), which can act on the tube set.

The monitoring apparatus 27, which has a memory 27A, a display apparatus 27B and an alarm unit 27C, is connected to the compliance-determining apparatus 28 via a data line 30.

The pressure in the extracorporeal blood circuit A is measured by a first pressure sensor 31, which measures the pressure in the blood supply line 5 downstream of the blood pump 6 and upstream of the blood chamber 2. In addition or alternatively to the pressure sensor 31 at the blood supply line 5, a pressure sensor (not shown in FIG. 1) can also be provided at the venous blood removal line 9, in particular upstream of the valve 12. This pressure sensor, like the pressure sensor 31 at the blood supply line 5, can be used to determine the compliance.

In the dialysate system B, the pressure is measured by a second pressure sensor 32, which measures the pressure in the first portion 16A of the dialysate removal line 16 downstream of the dialysate chamber 3 and upstream of the dialysate pump 17. It is also possible to provide only one pressure sensor, which is arranged such that the pressure is determined in the region in which the compliance is determined. That region can in particular include the whole dialyser.

The monitoring apparatus 27 and the compliance-determining apparatus 28 receive the signals from the first pressure sensor 31 via a signal line 33. The compliance-determining apparatus 28 receives the signals from the second pressure sensor 32 via a signal line 34. The measured pressure values are stored in the memory unit 27A of the monitoring apparatus 27.

Figure 2:
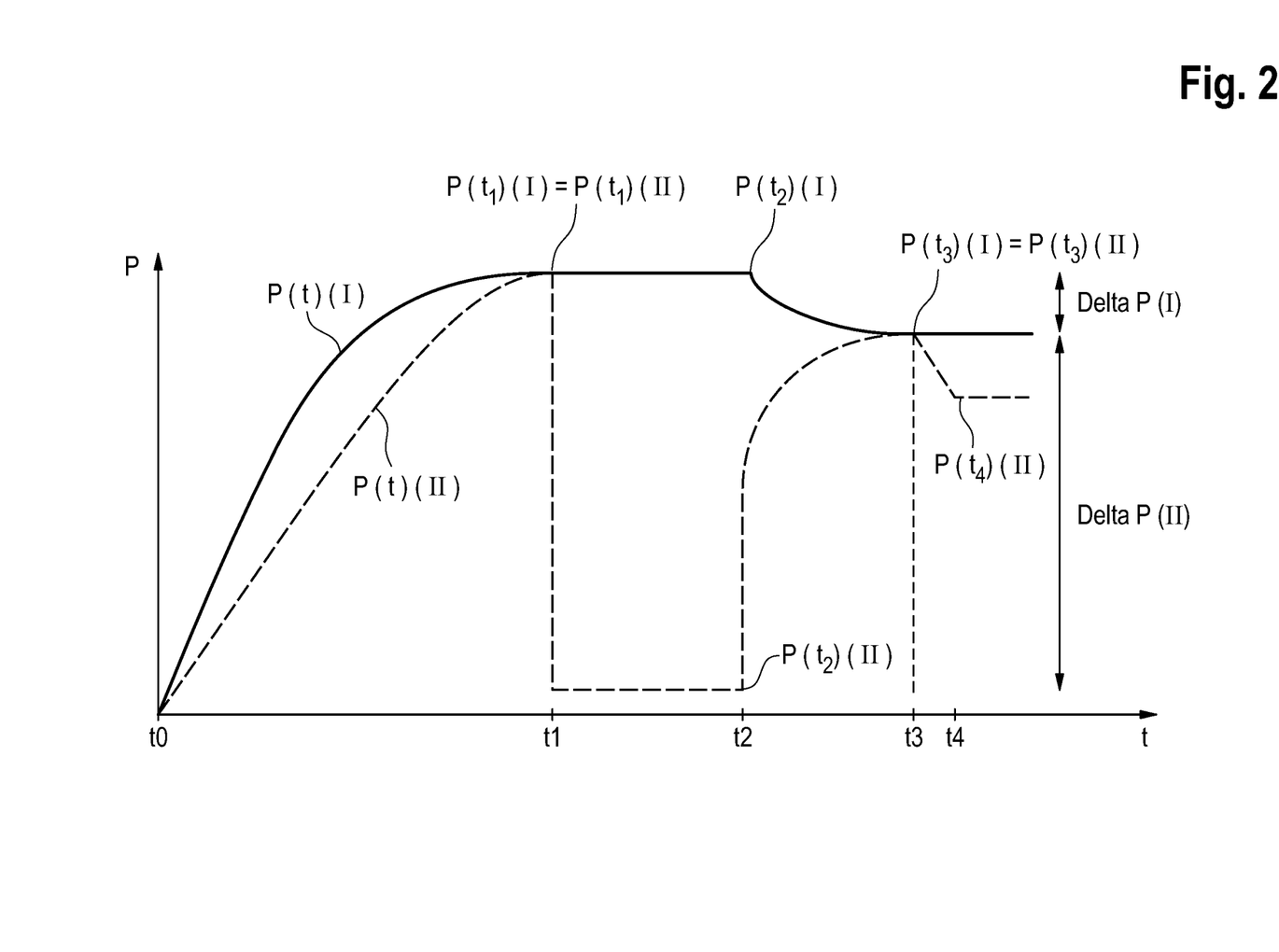
FIG. 2 is a schematic view of the profile over time of the pressure in the fluid system of the blood-treatment device when a leak has not occurred.
Figure 3:
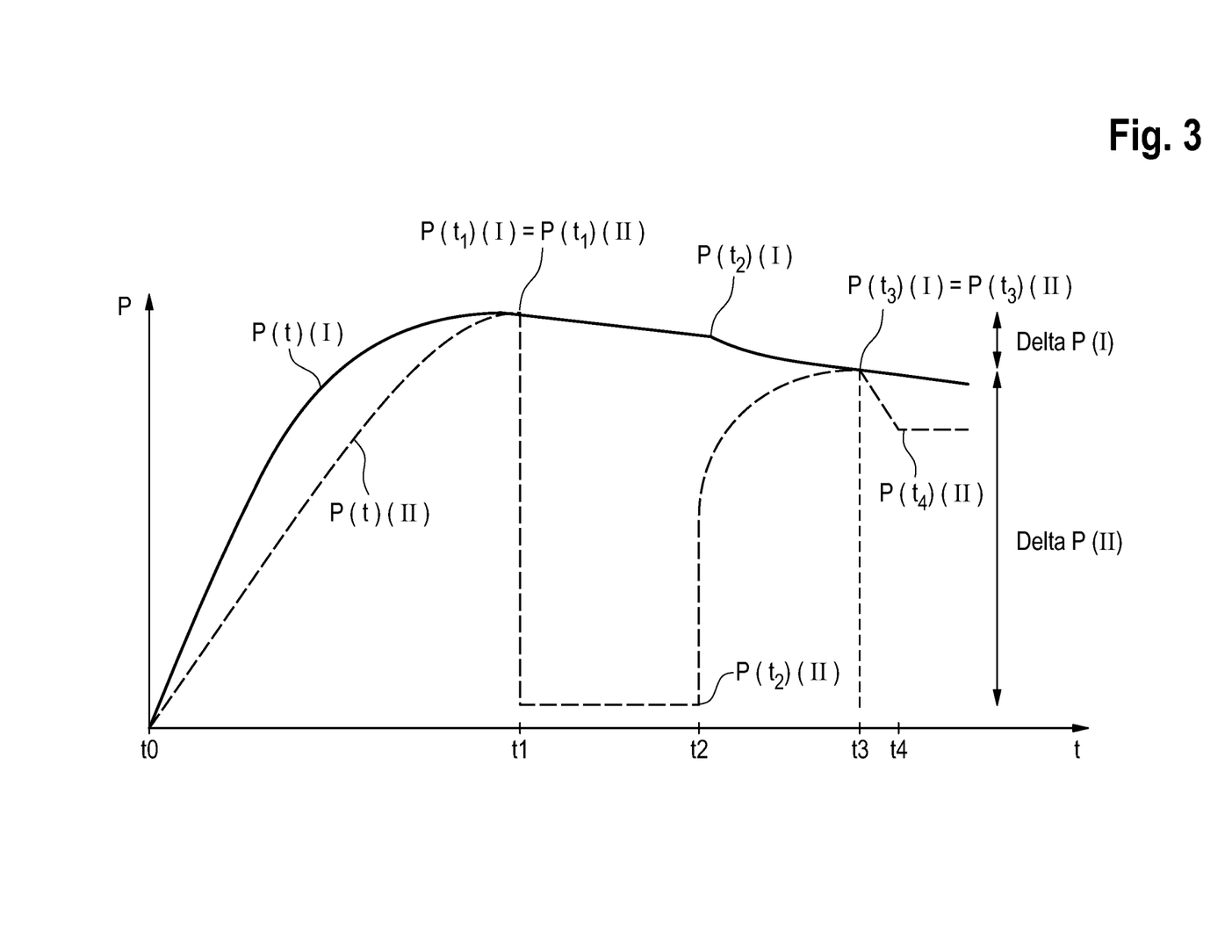
FIG. 3 is a schematic view of the profile over time of the pressure in the fluid system of the blood-treatment device when slight leakage has occurred.
Figure 4:
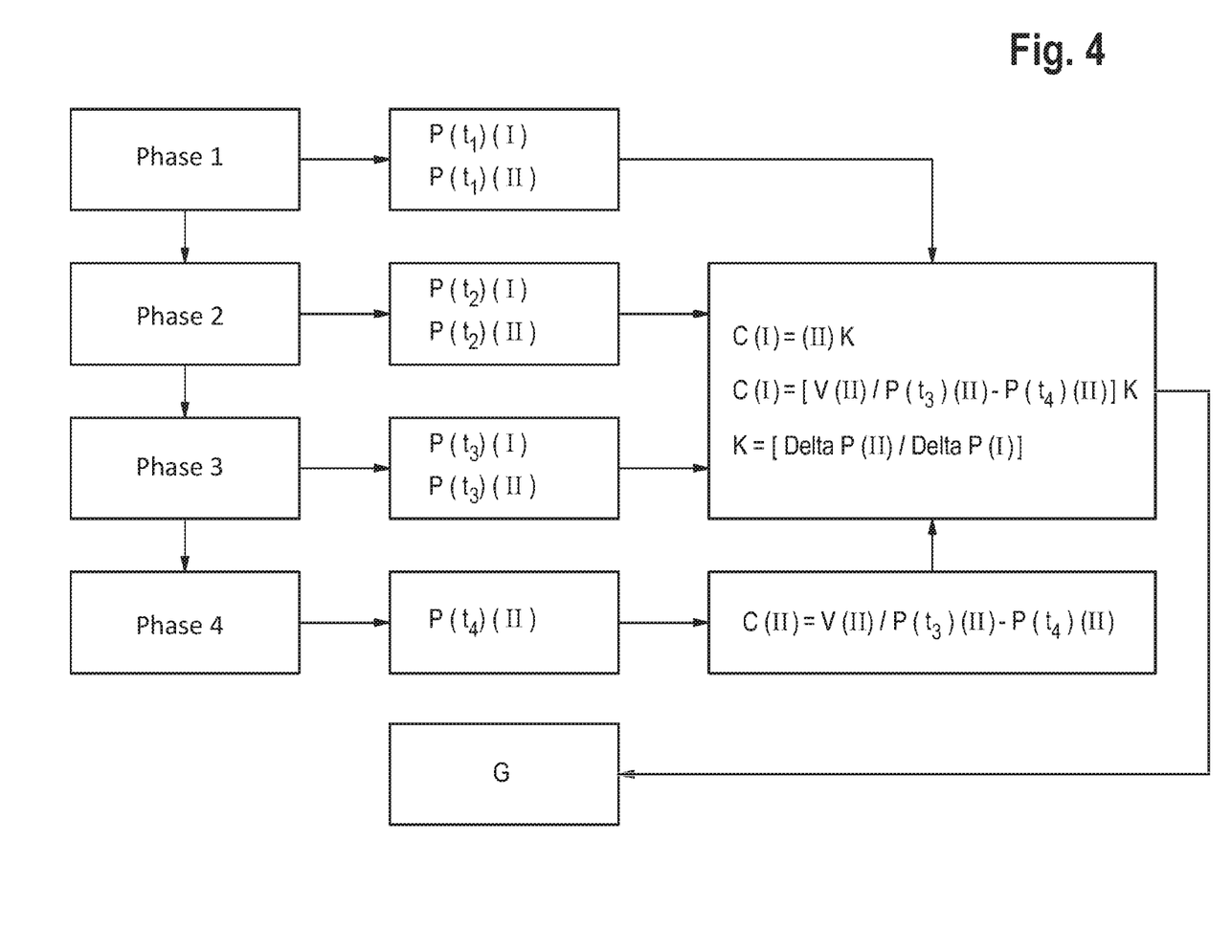
FIG. 4 is a flow diagram showing the individual phases of the monitoring process for one embodiment.

The monitoring apparatus 27 and the compliance-determining apparatus 28 control the individual components of the blood-treatment device as follows, in order to carry out the following method steps. FIGS. 2 and 3 show the pressure profile. FIG. 4 is a flow diagram showing the individual phases.

In the present embodiment, monitoring the blood-treatment device means testing the tightness of the fluid system. In the present embodiment, only part of the fluid system is tested for tightness. That part should be the part of the fluid system that includes the dialyser 1. Testing the tightness of the fluid system is based on a pressure hold test.

In order to carry out the pressure hold test, a part of the fluid system that is filled with liquid is separated from the fluid system of the blood-treatment device. To that end, the arterial valve 12, the valve 19 upstream of the dialyser 1 and the first and second bypass valves 22, 26 are first closed, and the second valve 20 downstream of the dialyser 1 is opened. The venous valve 8 does not need to be closed since the blood pump 6 is occlusive. The blood pump 6 is then started up in order to build up pressure in the closed volume of the fluid system (phase 1).

The excess pressure builds up in the portion of the blood supply line 5 between the blood pump 6 and the blood chamber 2, in the portion of the blood removal line 9 between the blood chamber 2 and the venous valve 12, in the blood chamber 2 and the dialysate chamber 3 and in the line portions between the dialysate chamber 3 and the valves 19, 20 that are upstream and downstream of the dialysate chamber 3. This part of the fluid system will be referred to hereinbelow as the first part I of the fluid system, in which the pressure hold test is to be carried out. Since the valve 20 downstream of the dialysate chamber 3 is open, excess pressure can also build up in the part of the fluid system that comprises the line portions downstream of the bypass valve 22 and upstream of the valve 26, as well as the dialysate pump 17 and the ultrafiltrate pump 24. This part of the fluid system will be referred to hereinbelow as the second part II of the fluid system.

The blood treatment device can also have a substitute pump 35, by means of which substitute can be supplied to the extracorporeal blood circuit A upstream or downstream of the blood chamber 2 via a substitute line 36. A further valve 37 is provided in the substitute line 36. In order to build up the pressure, it is also possible to operate the substitute pump 35, which supplies substitute to the blood supply or removal lines 5, 9 that are upstream or downstream of the blood chamber, instead of the blood pump 6.

In FIG. 1, the first part and the second part of the fluid system are denoted by I and II. The pressure measured by the first pressure sensor 31 in the first part I of the fluid system at time t is denoted by P(t) (I) and the pressure measured by the second pressure sensor 32 in the second part II of the fluid system at time t is denoted by P(t) (II).

FIG. 2 shows the profile of the pressure measured by the first and second pressure sensor 31, 32. This step is denoted as phase 1 in FIG. 4. The pressure in the extracorporeal blood circuit A measured by the first pressure sensor 31 is shown by a continuous line and the pressure in the dialysate system B measured by the second pressure sensor 32 is shown by a dashed line. In order to build up the pressure, the blood pump 6 and/or substitute pump 35 is operated such that a maximum permissible pressure limiting value and/or pressure gradient of the dialyser 1 is not exceeded, in order to avoid damaging the semi-permeable membrane 4. During pressure build-up, a pressure difference occurs between the pressure measured by the first and by the second pressure sensor 31, 32. In high-flux dialysers, the flow resistance of the membrane 4 of the dialyser 1 should be disregarded, in contrast to the low-flux dialysers. At time t1, the pressure difference is almost zero, since the blood pump 6 is running relatively slowly. Alternatively or in addition, the device can be configured to wait for a predetermined time and then use the pressure values at that time to determine the compliance. Alternatively or in addition, the system can wait until the gradient of the pressure change falls below a predetermined value and use the pressure value at that time for determining the compliance. In other words, the system does not necessarily have to wait until pressure equalisation is complete. The pressure P(t1) (I) and P(t1) (II) is measured (P(t1) (I)=P(t1) (II)). Low-flux dialysers can also be used, but pressure equalisation between the blood and dialysate chambers 2, 3 of the dialyser 1 takes longer in that case, that is to say the time at which the pressure P(t1) (I)=P(t1) (II) is later. The size of the pressure gradient is also dependent on the speed at which the liquid is pumped into or out of the fluid system.

When the pressure has successfully been built up, the valve 20 downstream of the dialysate chamber 3 is closed at time t1, in order to separate the first part I of the fluid system from the second part II (phase 2), so that the first and second part of the fluid system each form a closed volume. The monitoring apparatus 27, which in the present embodiment is a tightness-monitoring apparatus, can now carry out a pressure hold test in the first part I of the fluid system in order to test the tightness of that part of the fluid system, which comprises the portion of the blood supply line 5 between the blood pump 6 and the blood chamber 2, the portion of the blood removal line 9 between the blood chamber 2 and the venous tube clamp 12, the blood chamber 2 and the dialysate chamber 3 of the dialyser 1, as well as the portions of the dialysate supply line 14 and of the dialysate removal line 16 at which the couplings (not shown) of the dialyser are situated. If a substituate pump 35 is present, the tightness of the substituate line 36 downstream of the valve 37, for example of the check valve, is also tested.

If the first part I of the fluid system is tight, the pressure in that part of the fluid system remains constant (P(t1) (I)=P(t2) (I)). FIG. 2 shows the case where the system is tight. Consequently, the pressure in the first part I of the fluid system does not fall. FIG. 3 shows the case where the system is not tight. It can clearly be seen that the pressure in the first part I of the fluid system falls. A leak can be detected by testing whether the pressure falls below a specified limiting value in a specified time interval, or by measuring the time interval in which the pressure falls by a specified value.

During the pressure hold test in the first part I of the fluid system, the second part II of the fluid system is ventilated. To that end, the second bypass valve 26 is opened so that dialysate is able to flow into the drain 18. The pressure in the second part II of the fluid system thus falls sharply. A pressure P (II) which is greater than or equal to atmospheric pressure (FIGS. 2 and 3) but lower than the pressure in part I of the fluid system is established.

At time t2, at which ventilation of the second part II of the fluid system is complete, the second bypass valve 26 is closed again and the valve 20 downstream of the dialysate chamber 3 is opened again in order to produce a pressure equalisation between the first and second part of the fluid system (phase 3). The pressure in the first part I of the fluid system falls, while the pressure in the second part II of the fluid system increases. At time t3, the pressure equalisation is complete. At that time, the pressure P(t3) (I) is equal to the pressure P(t3) (II).

The compliance-determining apparatus 28 evaluates the pressure equalisation in time period Δt=t3−t2 as follows (FIG. 4). The compliance-determining apparatus 28 determines the pressure drop delta P (I) in the first part I of the fluid system from the difference between the pressure P(t2) (I) at time t2 and the pressure P(t3) (I) at time t3. In addition, the apparatus 28 determines the pressure difference delta P (II) of the second part (II) of the fluid system from the pressure P(t3) (II) at time t3 and the pressure P(t2) (II) at time t2. The compliance-determining apparatus 28 then calculates the ratio K between the compliance C (I) in the first part I of the fluid system and the compliance C (II) in the second part (II) of the fluid system from the ratio of the pressure changes delta P, in accordance with the following equation:

$$K=C(I)/C(II)=\text{delta } P(II)/\text{delta } P(I) \qquad \text{Equation (1)}$$

When the pressure equalisation has taken place at time t3, the valve 20 downstream of the dialysate chamber 3 is closed again and the ultrafiltrate pump 24 or the dialysate pump 17 is operated briefly so that a specific volume of dialysate is removed from the second part II of the fluid system, which results in a pressure drop. Removing dialysate by means of the ultrafiltrate pump 24 instead of the dialysate pump 17 has the advantage that even a defined small volume of dialysate can be removed. A specific liquid volume can also be supplied or removed by means of a known syringe pump, which is distinguished in that it conveys small volumes with great accuracy. The supply or removal of liquid by means of a heparin pump, which is generally already present in blood-treatment devices, is therefore also possible.

The use of the ultrafiltrate pump is therefore suitable since it is intended to pump away a very defined liquid volume during treatment and is therefore suitable in terms of its construction for pumping away well-defined flows. Alternatively, however, it is possible to use architectures which are known to a person skilled in the art. For example, a dialysate pump having a flow meter, for example having a Coriolis dynamometer, can also be used for pumping away the liquid. The ultrafiltrate pump can be a membrane pump.

At time t4, a pressure P(t4) (II) is established in the second part II of the fluid system (phase 4). The apparatus 28 calculates the compliance C (II) in the second part II of the fluid system from the known volume V (II) of the second part II of the fluid system and the ascertained pressure difference P(t3) (II)−P(t4) (II), in accordance with the following equation:

$$C(II)=V(II)/(P(t3)(II)-P(t4)(II)) \qquad \text{Equation (2)}$$

Since the ratio K of the compliance between the first and second part of the fluid system is known, the apparatus 28 can determine the compliance of the first part of the fluid system. The compliance C is determined in accordance with the following equation:

$$C(I)=C(II)K=[V(II)/P(t3)(II)-P(t4)(II)]K$$

$$K=[\text{delta } P(II)/\text{delta } P(I)] \qquad \text{Equation (3)}$$

The monitoring apparatus 27 receives the value of the compliance C (I) via the data line 30 and monitors the blood-treatment device depending on the compliance.

The blood-treatment device can further be configured to carry out the above-described method in fluid systems having slight leakage too, see the curves in FIG. 3. In this embodiment, the compliance-determining apparatus can be configured to determine one, a plurality of or all the pressure values at times t1 to t4 from the profiles of the curves over time by extrapolation. In particular, this can be carried out for time t4. Such an extrapolation can improve the result if the pressure cannot be determined at the predetermined time. This will be described by way of example using the example of t4: Time t4 is the time at which the pump for removing the volume is stopped. However, the system then requires a certain amount of time to receive or process the pressure data, or those data are received only at specific time slices. If they are not received precisely at time t4, that value is not known. In addition, if the pressure value falls slowly on account of a small leak, the correct pressure value at time t4 can be determined by extrapolation of the later pressure values since either time t4 is known exactly or the point of intersection of the descending curve between t3 and t4 with the curve according to t4 is determined.

For the pressure hold test which is carried out by the monitoring apparatus 27, a limiting value G is fixed. That limiting value is set depending on the compliance C (FIG. 4).

In the present embodiment, a limiting value which applies to an ideal system of fixed volume is first assumed. That limiting value, which is stored in a memory 27A of the control and/or monitoring apparatus 27, is corrected using a correction factor which is determined depending on the previously ascertained compliance C (I). For example, different correction factors can be allocated to individual compliance values. These correction factors are set such that the assumed limiting value is increased as the compliance increases and reduced as the compliance falls.

The monitoring apparatus 27 reads the pressure P(t1) (I) and P(t2) (I) measured by the first and second pressure sensors 31, 32 from the memory 27A and compares the pressure difference ΔP in the specified time interval Δt=t2−t1 with the limiting value G ascertained depending on the compliance C(I). If the value for the pressure difference ΔP is less than the limiting value, it is concluded that the system is tight. This proper state can be displayed on the display apparatus 27B. If, on the other hand, the value for the pressure difference ΔP is greater than the limiting value, that is to say the pressure in the specified time interval Δt=t2−t1 has fallen too greatly, the alarm unit 27C emits an alarm. In this case, the monitoring apparatus 27 can also intervene in the machine control system in order to stop the blood treatment.

The monitoring apparatus 27 additionally calculates the leakage rate Q from the previously measured pressure drop Δp in the time interval Δt=t2−t1, in accordance with the following equation:

$$Q(I)=C(I)\Delta p/\Delta t \qquad \text{Equation (4)}$$

The time interval Δt=t2−t1 in which the measured values are recorded can be a fixed time interval. It is, however, also possible for the rate of change dp/dt in the pressure (gradient of the curve) to be detected, the measured values then being ascertained when the signal is sufficiently stable, that is to say the rate of pressure change is less than a limiting value.

The leakage rate Q (I) can also be compared with a specified limiting value. If the leakage rate is greater than the limiting value, the alarm unit 27C emits an alarm.

The monitoring apparatus 27 further tests whether the compliance C in a part I of the fluid system that includes the dialyser is greater than a specified limiting value. If the compliance C (I) is greater than the limiting value, it is concluded that the dialyser 1 has not been sufficiently ventilated. This can likewise be displayed on the display apparatus 27B.

In all the embodiments, the pressure-based monitoring is carried out depending on the compliance C of the fluid system, so that reliable monitoring is possible even if the compliance in the system changes, for example as a result of air pockets in particular in the dialyser, or the compliance of the system is not known beforehand. The treatment device can be configured such that the compliance is determined in the preparation mode and/or treatment mode. The adjustment of limiting values or parameters can take place automatically.

The following provides a detailed description of the point at which the compliance is determined and the treatment device is monitored.

The known blood-treatment devices provide a treatment mode and a preparation mode, which precedes treatment, in preparation for the treatment. During the blood treatment, the part of the fluid system that comprises the blood supply line 5, the blood chamber 2 of the dialyser 1 and the blood return line 9 is filled with blood conveyed by the blood pump 6. In the preparation mode, which precedes the blood treatment, that part of the fluid system is not filled with blood. The blood-treatment device has an apparatus that is able to detect the extent to which that part of the fluid system is filled with blood. This apparatus can be a blood detector 38 which is provided at the blood supply line 5. As soon as the blood detector 38 detects blood, the blood-treatment device is in the treatment mode. The blood detector can be an optical detector which determines the optical density of the medium in the tube system. It can thus be sufficient that the blood detector is able to distinguish blood from the preparation liquid.

The monitoring apparatus 27 is configured such that the determination of the compliance takes place in the preparation mode and the compliance-dependent, pressure-based monitoring takes place in the preparation mode and/or the treatment mode. In the preparation mode, the valve 12 can be closed and the blood pump 6 does not need to be operated, so that the part of the fluid system in question can form a closed volume. In the preparation mode, the dialyser 1 is part of the fluid system, so that part of the fluid system which includes the dialyser can be monitored. If the compliance has been determined in the preparation mode, monitoring can take place in the preparation mode or in the treatment mode. The above-described initial pressure hold test, for example, takes place in the preparation mode. Further compliance-dependent pressure hold tests can also take place in the treatment mode. Instead of a pressure hold test, which is described only as an example of monitoring, any monitoring parameters that are relevant for the monitoring can be fixed or adjusted in the treatment mode depending on the compliance determined in the preparation mode.

Figure 5:
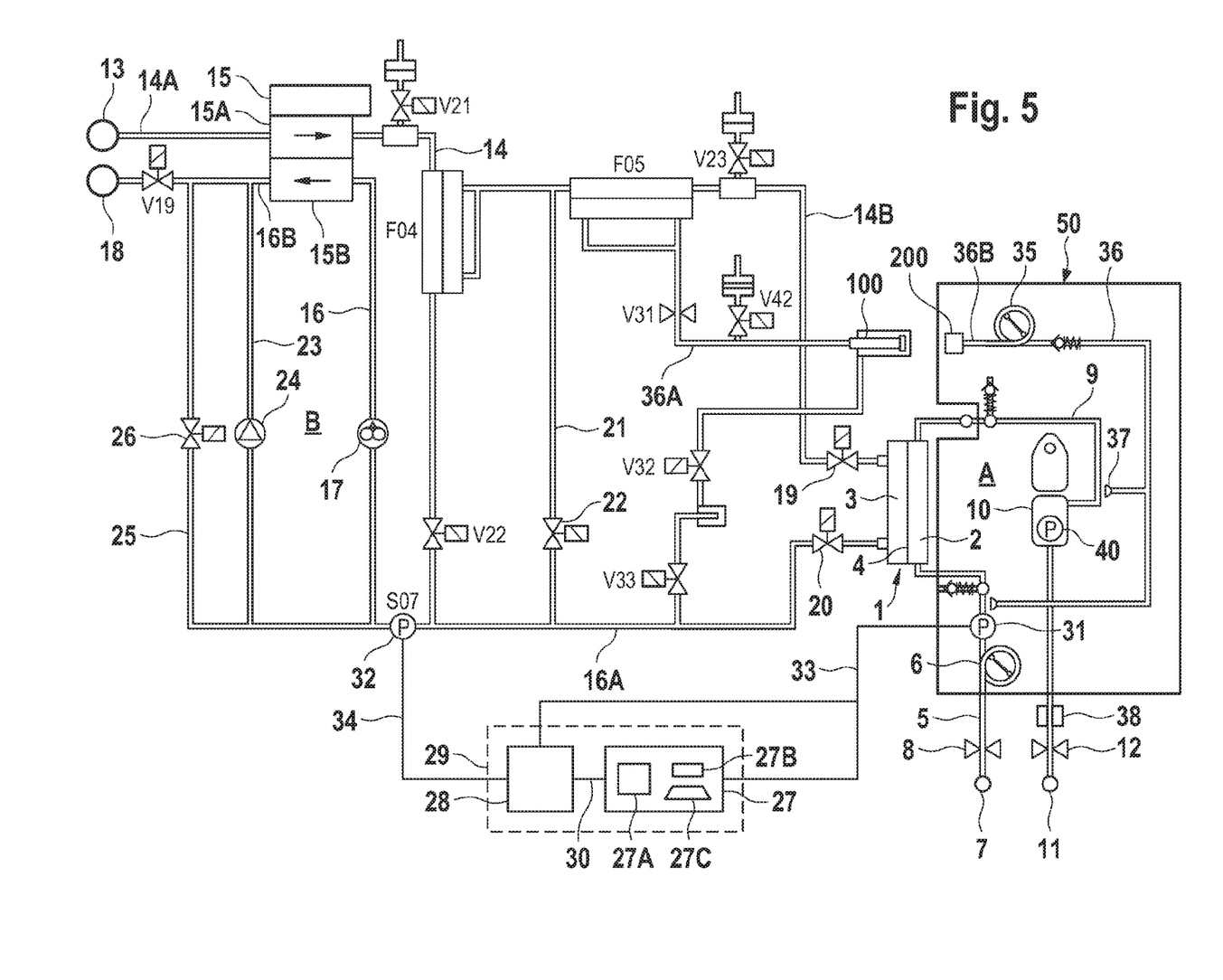
FIG. 5 shows a further embodiment of a blood-treatment device according to the invention.

FIG. 5 shows a further embodiment of a blood-treatment device according to the invention, in which the extracorporeal blood circuit A is in the form of a disposable cassette 50. In FIG. 5, those elements which correspond to those of FIG. 1 have been provided with the same reference numerals. With regard to those elements, the description thereof is not repeated and reference is made to the statements made in connection with FIG. 1. Only possible additions or further embodiments or differences between the two embodiments are described here.

The treatment device can have at least one sterile filter F04. FIG. 5 shows an embodiment having two sterile filters F04 and F05. The sterile filters serve to further purify the dialysate provided and/or prepared in the dialysate source 13. In FIG. 5, the machine-side portion 36A of the substituate line 36 has not yet been connected to the cassette-side line portion 36B. A connector 100 can be provided in the treatment device for the fluid connection, which connector is able to cooperate with a connector 200 of the disposable cassette.

The treatment device can additionally have further lines between the dialysate supply line 14 and the dialysate removal line 16. These lines, which are not shown in more detail in FIG. 5, can start, for example, from the sterile filter F04 or the sterile filter F05 and lead to the dialysate removal line 16.

For determining the compliance, the treatment device has all the necessary closure elements for fluidic connections, in order to close off the volumes in which a pressure is built up. These elements, for example valves, shown by way of example are provided with the reference numerals V19, V21, V22, V23, V31, V32, V33 and V42 in FIG. 5.

In contrast to separate blood tube sets, the disposable cassette 50 has a common housing body for the arterial blood supply line 5 and the venous blood removal line 9, in which housing body at least portions of the two lines run. Furthermore, at least a portion of the substituate line 36 can also extend in the cassette 50. The cassette can also have a branch of the substituate line 36 opening into the venous blood line 9 (post-dilution) and a branch of the substituate line 36 opening into the arterial blood line 6 (pre-dilution). Such a line system can also be embodied in a blood tube set.

The valves at the points at which the substituate line 36 opens into the venous and arterial blood line 5, 9 can be formed in the cassette, for example the valve 37. As the valve, the cassette can have a film which is pressed by a machine-side actuating member (not shown in FIG. 5) against a rigid body in the cassette in order to close a fluid channel. The treatment device can also have a pressure sensor 40, which is arranged at the venous blood line 9, in particular at the air separation chamber 10 of the venous line 9. The pressure value of this sensor can likewise be evaluated in order to determine the compliance. For measuring the pressure, the treatment device can have a pressure sensor which measures the fluid pressure acting on a film of the cassette 50.

In the case of a cassette in which the arterial and venous blood lines are brought together in one component, it can be possible that the measures necessary for ventilating the dialyser 1 cannot be carried out. For example, because of the relatively short length of the tubes, it may not be possible for the dialyser to be rotated for ventilation purposes. Taking the compliance into account for determining one or more operating parameters of the treatment device may therefore be of importance particularly in the case of disposable cassettes. The number of alarms and/or error messages can thereby be reduced, for example, whereby the use efficiency, that is to say the time in which a dialysis operation can be carried out, can also be increased.

Figure 6A:
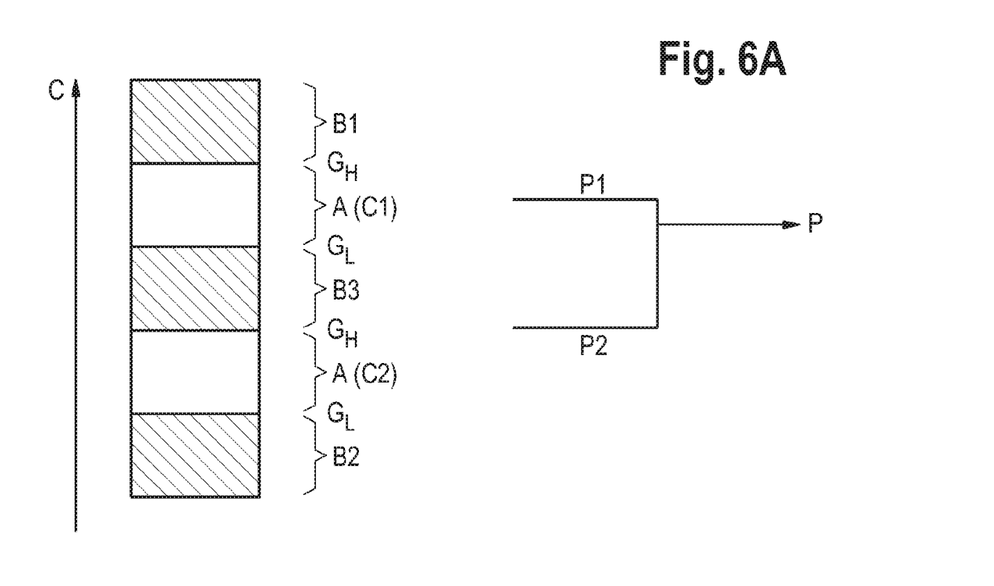
FIGS. 6A and 6B are diagrams showing the setting of parameters for monitoring the treatment.
Figure 6B:
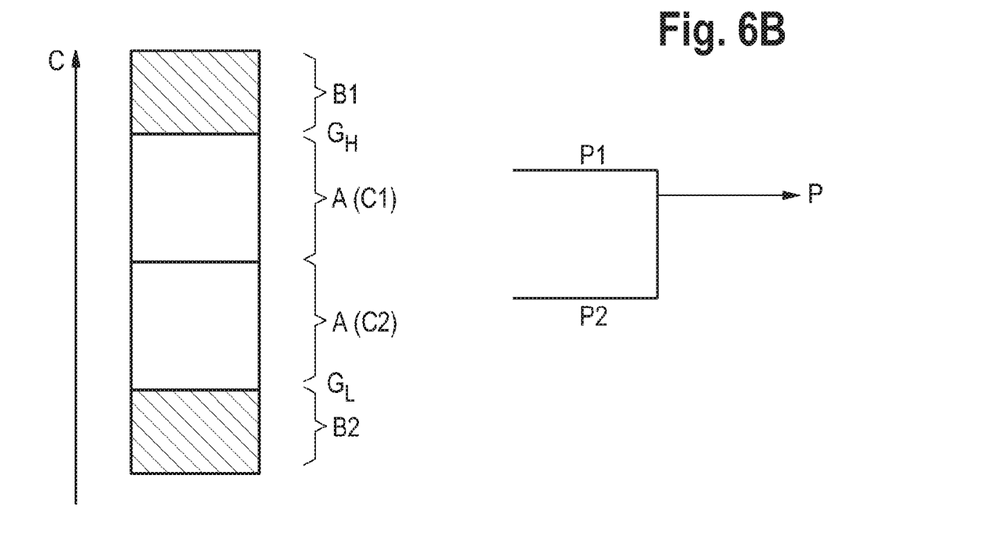

FIGS. 6A and 6B show diagrams to illustrate the setting of parameters for monitoring the treatment depending on the compliance. In both embodiments, an upper and a lower limiting value $G_H$ and $G_L$ are set in each case depending on the compliance. The limiting values $G_H$ and $G_L$ each delimit a permissible working range A(C1) for a compliance C1 or a permissible working range A(C2) for a compliance C2, wherein the compliance C1 is greater than the compliance C2. Outside the working ranges A(C1) and A(C2), upper and lower alarm ranges B1, B2, B3 (FIG. 6A) and upper and lower alarm ranges B1 and B2 (FIG. 6B) are set.

FIG. 6A illustrates the choice of parameters for the case where the upper and lower working range A(C1) and A(C2) are two separate ranges, between which there is an alarm range B3, and FIG. 6B illustrates the case where the upper and lower working range A(C1) and A(C2) form a common working range.

If the compliance C lies within the alarm range B1, for example, it can be concluded that the ventilation of the fluid system, in particular of the dialyser, is not sufficient. If the compliance lies within the alarm range B3, for example, it can be concluded that an unknown dialyser is being used. If the compliance C lies within the alarm range B2, for example, it can be concluded that the determination of the compliance was not successful, since the compliance is expected to lie above that range. These operating states can be displayed on the display apparatus 27B. Within the working ranges A(C1) and A(C2), the parameterisation P1 and P2 can take place. For example, depending on the compliance C, a maximum pressure drop $\Delta P1$ or $\Delta P2$ can be set, which may not be exceeded in a pressure hold test, if it is assumed that the fluid system is tight. For the working range A(C1), depending on the compliance (C), a smaller maximum pressure drop $\Delta P1$ is set for a larger value of the compliance C1 than for a smaller value of the compliance C2. Alternatively, it is also possible to set a time interval in which the pressure falls by a specified value.

The invention claimed is:

1. A medical treatment device comprising
a central control and arithmetic apparatus comprising a monitoring apparatus and a compliance-determining apparatus;
at least one pump for conveying at least one liquid into and/or out of a fluid system; and
at least one pressure sensor for measuring a pressure in at least part of the fluid system, wherein
the monitoring apparatus and the compliance-determining apparatus are configured to receive sensed pressure signals from the at least one pressure sensor via a signal line,
the monitoring apparatus comprises a memory, wherein the monitoring apparatus is configured to monitor the fluid system based on evaluations of sensed pressure in the fluid system, and to store sensed pressure signals in the memory,
the compliance-determining apparatus is configured to evaluate pressure signals sensed by the at least one pressure sensor and determine a compliance of the fluid system based on the evaluating, and
the compliance-determining apparatus cooperates with the monitoring apparatus in such a manner that at least one limiting value is set based on the compliance of the fluid system, and pressure-based monitoring takes place by the monitoring apparatus based on comparing pressure signals stored in the memory, with the limiting value, such that reliable monitoring is possible even for a fluid system that has a compliance that changes.

2. The medical treatment device according to claim 1, wherein the medical treatment device provides a treatment mode and a preparation mode that precedes the treatment mode, wherein the monitoring apparatus is configured such that the compliance is determined in the preparation mode and the compliance-dependent, pressure-based monitoring takes place in the preparation mode and/or in the treatment mode.

3. The medical treatment device according to claim 2, configured such that the compliance-dependent, pressure-based monitoring takes place in the treatment mode.

4. The medical treatment device according to claim 1, wherein the monitoring apparatus is a tightness-monitoring apparatus configured to monitor pressure in the fluid system, wherein, when there is a change in the pressure depending on the compliance, it is concluded that the fluid system is not tight.

5. The medical treatment device according to claim 4, wherein the tightness-monitoring apparatus is configured to compare an amount of change in pressure over a specified time interval with the at least one limiting value, and, it is concluded that the system is not tight if the amount of change in the pressure is greater than the at least one limiting value.

6. The medical treatment device according to claim 1, wherein, when a volume of a liquid enclosed in the fluid system is changed, the compliance of the fluid system is determined on the basis of the pressure change resulting from the change in volume.

7. The medical treatment device according to claim 1, wherein the compliance-determining apparatus is configured to: determine a ratio K of a compliance C (I) in a first part (I) of the fluid system to a compliance C (II) in a second part (II) of the fluid system; and either determine the compliance C (II) in the second part (II) of the fluid system from the compliance C (I) in the first part of the fluid system and the ratio K, or determine the compliance C (I) in the first part (I) from the compliance C (II) in the second part of the fluid system and the ratio K.

8. The medical treatment device according to claim 7, wherein the compliance-determining apparatus is configured to determine the ratio K by determining the ratio of the pressure change in the first part of the fluid system to the pressure change in the second part of the fluid system in the case of a pressure equalisation between the first and second parts of the fluid system.

9. The medical treatment device according to claim 1, wherein the treatment device has at least one receiver for replaceably receiving at least part of the fluid system.

10. The medical treatment device according to claim 1, wherein the medical treatment device is an extracorporeal blood-treatment device that has a fluid system comprising a dialyser divided by a semi-permeable membrane into a blood chamber and a dialysate chamber, a blood supply line leading to the blood chamber and a blood removal line coming from the blood chamber, a dialysate supply line leading to the dialysate chamber and a dialysate removal line coming from the dialysate chamber, and the compliance-determining apparatus is configured such that the compliance C (I) is determined in a first part (I) of the fluid system that comprises a portion of the blood supply line, a portion of the blood removal line, the blood chamber, and the dialysate chamber of the dialyser.

11. The medical treatment device according to claim 10, wherein the compliance-determining apparatus is configured to determine a ratio K of compliance C (I) in the first part (I) of the fluid system to the compliance C (II) in a second part (II) of the fluid system, that does not include the first part of the fluid system, and the compliance C (I) in the first part of the fluid system is determined from the compliance C (II) in the second part of the fluid system and the ratio K of the compliance in the first and second parts of the fluid system.

12. The medical treatment device according to claim 10, wherein the medical treatment device has a dialysate source for fresh dialysate, a drain for used dialysate, a blood pump for conveying blood, a dialysate pump for conveying dialysate, and an ultrafiltration apparatus having an ultrafiltration line leading from a first portion of the dialysate removal line to a second portion of the dialysate removal line and an ultrafiltration pump for withdrawing ultrafiltrate through the ultrafiltrate line, and configured such that, when a specified volume of liquid is removed from the second part (II) of the fluid system, the compliance-determining apparatus determines the compliance C (II) in a second part (II) of the fluid system on the basis of the pressure change in the second part of the system, wherein the dialysate pump and/or the ultrafiltration pump is/are operated in order to remove dialysis fluid from the second part of the fluid system into the drain.

13. A method for monitoring a medical treatment device that has a fluid system that encloses at least one volume that can be filled with a liquid, in which monitoring is based on evaluations of pressure in the fluid system, wherein a compliance in the fluid system is determined based on evaluations of pressure in the fluid system, at least one limiting value is set based on the compliance, and a pressure-based monitoring takes place depending on the compliance of the fluid system by comparing evaluations of the pressure to the at least one limiting value.

14. The method according to claim 13, wherein a pressure in the fluid system is monitored, an amount of change in the pressure in a specified time interval is compared with the at least one limiting value, and it is concluded that there is a leak if the amount of change in the pressure is greater than the at least one limiting value.

15. The method according to claim 13, wherein a treatment mode and a preparation mode preceding the treatment mode, are provided, the determination of the compliance takes place in the preparation mode, and the compliance-dependent, pressure-based monitoring takes place in the preparation mode and/or in the treatment mode.

* * * * *